United States Patent [19]

Vaidyanathan

[11] 4,453,027
[45] Jun. 5, 1984

[54] ADIABATIC PROCESS FOR THE NITRATION OF HALOBENZENES

[75] Inventor: Kumbakonam R. Vaidyanathan, St. Louis, Mo.

[73] Assignee: Monsanto Company, St. Louis, Mo.

[21] Appl. No.: 448,456

[22] Filed: Dec. 10, 1982

[51] Int. Cl.³ .............................................. C07C 79/12
[52] U.S. Cl. ................................................. 568/937
[58] Field of Search .............................. 568/937, 938

[56] References Cited

U.S. PATENT DOCUMENTS

| | | | |
|---|---|---|---|
| 3,077,502 | 2/1963 | Leib | 260/646 |
| 3,927,127 | 12/1975 | Damiano | 260/646 |
| 3,928,395 | 12/1975 | Seha et al. | 260/369 |
| 3,928,476 | 12/1975 | Shimada et al. | 260/646 |
| 3,966,830 | 6/1976 | Shimada et al. | 568/938 X |
| 3,979,467 | 9/1976 | Schumacher | 568/938 X |
| 4,112,005 | 9/1978 | Thiem et al. | 568/937 X |

FOREIGN PATENT DOCUMENTS 678000 12/1960 Canada ................................ 568/937

OTHER PUBLICATIONS

Bieber et al., Ind. & Eng. Chem., vol. 49, No. 5, May 1957, pp. 832 to 837 (TP1A58) Copy in Sci. Lib. and 568–937.

Primary Examiner—Leland A. Sebastian
Attorney, Agent, or Firm—Wendell W. Brooks; James C. Logomasini; Arnold H. Cole

[57] ABSTRACT

Nitrohalobenzenes are prepared adiabatically using an excess of sulfuric acid.

5 Claims, 1 Drawing Figure

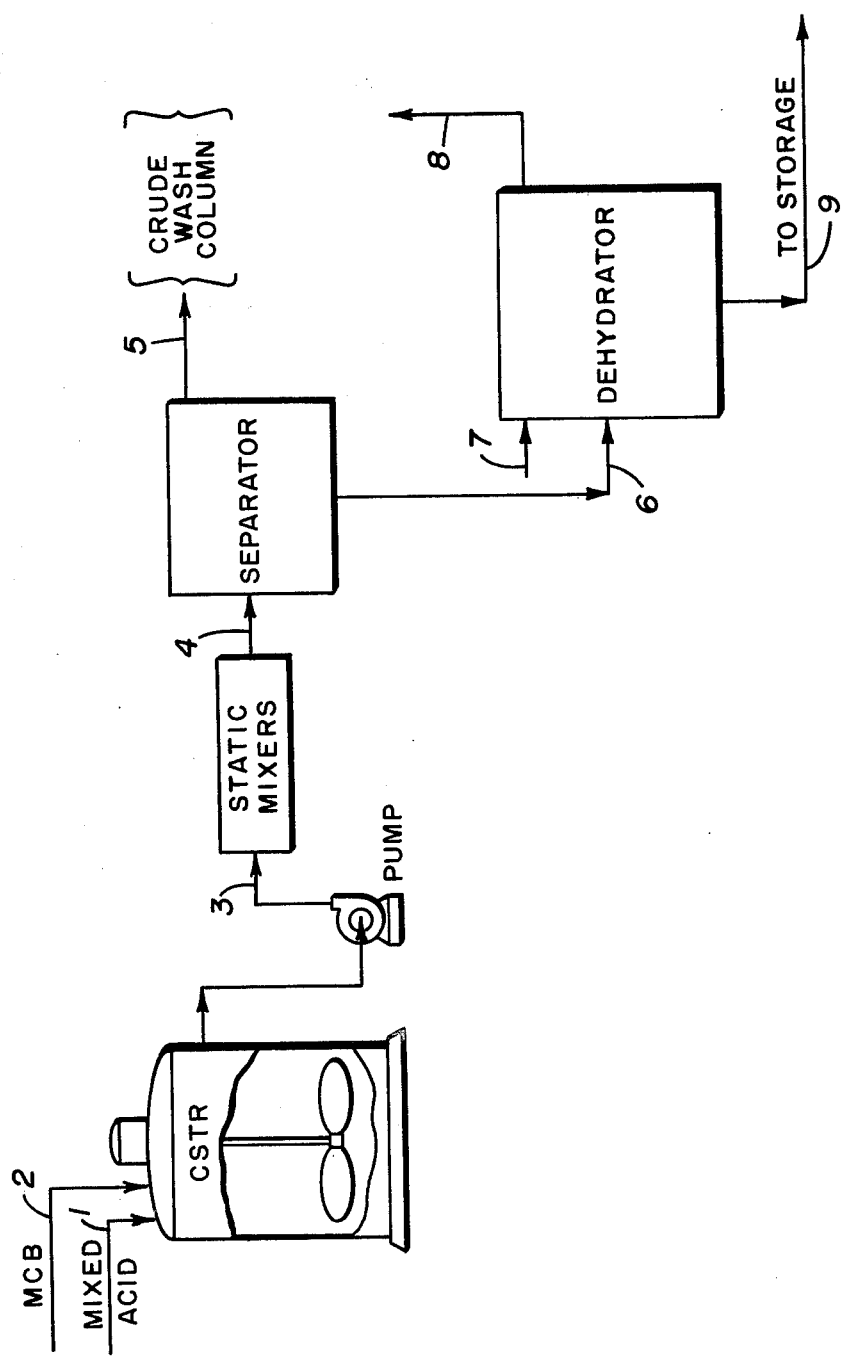

ADIABATIC PROCESS FOR THE NITRATION OF HALOBENZENES

BACKGROUND OF THE INVENTION

A. Field of the Invention

The invention relates to an improved process for the preparation of nitrohalobenzenes by the nitration of the corresponding halobenzene.

B. The Prior Art

It is well known to produce nitrohalobenzenes (such as nitrochlorobenzene) from halobenzenes (such as monochlorobenzene) by reacting a halobenzene with nitric acid and a second acid selected from the group consisting of sulfuric acid, phosphoric acid, sulfonic acid and mixtures of the above.

Typical of such processes is that described by U.S. Pat. No. 3,077,502, a commercial translation of which is a three-reactor conversion wherein sulfuric acid and nitric acid, as well as monochlorobenzene, is fed into the first reactor, with heat being removed and temperature maintained at about 45° C. Residence time is about 45 minutes in the first reactor, and the conversion level based on nitric acid is 85–90%. The contents of the first reactor overflow into the second reactor wherein temperature is maintained at about 65° C. Residence time in the second reactor is about 45 minures, and the conversion level is about 90–95%. The contents of the second reactor overflow into a third reactor where temperature is maintained at about 70° C. Residence time is about 60 minutes and conversion based on nitric acid is close to about 99.5%.

Sulfuric acid, at a starting mole ratio to nitric acid of about 2/1, takes up the water generated during the course of the reaction, and its concentration drops from about 85% to about 73.5% at the end of the reaction. The spent acid is removed from the product stream in an oil-acid separator, and is pumped to an acid dehydrator. The dehydrated sulfuric acid at about 85% concentration is returned to the process.

Any method for increasing the efficiency of this production would be a significant advance in the art and is an object of this invention.

SUMMARY OF THE INVENTION

According to the instant invention, a halobenzene such as monochlorobenzene is reacted with nitric acid and a carrier acid selected from the group consisting of sulfuric acid, phosphoric acid, sulfonic acid and mixtures thereof by bringing together over two moles of the carrier acid and about one mole of nitric acid with an excess of halobenzene so as to permit the excess of carrier acid to serve as a heat sink (holding and storing heat) from which the water produced during nitration can be flashed off under vacuum in a dehydration step following its separation from the crude nitrohalobenzene. The dehydration step employs the stored heat of reaction and thereby saves energy.

In the detailed description, reference will be made to the Drawing in which the FIGURE is a schematic flow sheet of a preferred embodiment of this invention.

DETAILED DESCRIPTION OF THE INVENTION

While the carrier acid may be sulfuric acid, phosphoric acid, sulphonic acid or mixtures thereof, it will be referred to hereafter as the preferred sulfuric acid.

An excess of sulfuric acid in the amount of about four (4) moles of sulfuric to one (1) of nitric, preferably, is used so as to permit the excess of sulfuric acid to serve as a heat sink from which the water produced during nitration can be flashed off under vacuum following its separation from the crude nitrochlorobenzene.

By "about", as applied to mole ratios is meant ±1.

In accordance with a preferred embodiment, a nitration acid mixture is preferred combining the required amount of about 77–78% by weight of the preferred sulfuric acid with 22–23% nitric acid so that the molar ratio sulfuric acid to nitric acid is about 4/1. Since the excess of acid serves as a heat sink, mole ratios greater or less than 4/1 can also be used depending on the desired final temperature of the reaction mass. The nitration acid mixture is preferably introduced into a reactor or series of reactors of the CSTR, tubular or combined flow types along with about 1.1 moles of a monohalobenzene such as monochlorobenzene. A desirable reaction product, at a temperature of about 100°–110° C., is conveyed to a separator after which the spend acid is flashed off under vacuum to remove the water produced in the reaction (a mole of water for each mole of nitric acid reacted). The acid is then returned to the process. The crude nitrohalobenzene (nitrochlorobenzene) is then washed free of acid. It will typically contain about 58% paranitrochlorobenzene, depending upon the extent of reaction and heat released when the reactants are brought together.

Referring now in detail to the Drawing, the FIGURE represents a flow sheet of a preferred embodiment of this invention. Monochlorobenzene and the mixed acid is fed to the continuously stirred reactor where the adiabatic nitration takes place. The reactor product stream is fed to a pump and a static mixer for further reaction, and thereafter conveyed to a separator where the crude nitrochlorobenzene is separated from the acid. The nitrochlorobenze is subsequently washed and the acid is conveyed to a dehydrator where water is flashed off and the acid conveyed to storage.

EXAMPLE

The nitration reaction was conducted according to the flow sheet shown in the drawing using the quantities of raw materials shown in Table I, thereby producing the product stream shown in column 5.

TABLE I

| Stream Component | 1 | 2 | 3 | 4 | 5 | 6 | 7 | 8 | 9 |
|---|---|---|---|---|---|---|---|---|---|
| Nitric Acid | 40.0 | — | 20.0 | 0.03 | 0.015 | 0.015 | — | — | — |
| Sulfuric Acid | 245.4 | — | 245.4 | 245.40 | — | 245.40 | — | — | 245.4 |
| Water | 73.1 | — | 78.8 | 84.52 | — | 84.52 | — | 11.42 | 73.1 |
| MCB | — | 75.1 | 39.3 | 3.63 | 3.63 | — | 5.0 | 5.0 | — |
| NCB | — | — | 50.0 | 99.92 | 98.6 | 1.32 | — | 1.32 | — |
| TOTAL | 358.5 | 75.0 | 433.5 | 433.5 | 102.25 | 331.25 | 5.0 | 17.74 | 318.5 |

TABLE I-continued

| Stream Component | 1 | 2 | 3 | 4 | 5 | 6 | 7 | 8 | 9 |
|---|---|---|---|---|---|---|---|---|---|
| Temp. (°C.) | 45 | 45 | 78 | 110 | | | | | |

McB = monochlorobenzene
NCB = nitrochlorobenzene

I claim:

1. In a continuous process for the production of nitrohalobenzene from halobenzene by reacting a halobenzene with nitric acid and a carrier acid selected from the group consisting of sulfuric acid, phosphoric acid, sulfonic acid and mixtures thereof, the improvement comprising bringing together more than two moles of the carrier acid and about 1 mole of nitric acid with an excess of 1 mole of the halobenzene.

2. The process improvement of claim 1 where the halobenzene is monochlorobenzene.

3. The process improvement of claim 1 wherein the carrier acid is sulfuric acid.

4. In a continuous process for the production of nitrohalobenzene from monohalobenzene by reacting monohalobenzene with nitric acid and sulfuric acid and thereafter separating the monohalobenzene from the product stream, the improvement comprising bringing together the sulfuric acid, the nitric acid and the monohalobenzene in a mole ratio of about 4/1/1.1, thereby to provide a product stream of separation having a temperature of about 100°–110° C.

5. The process improvement of claim 4 wherein the monohalobenzene is monochlorobenzene.

* * * * *